US00PP20074P2

(12) United States Plant Patent

Isobe et al.

(10) Patent No.: US PP20,074 P2

(45) Date of Patent: Jun. 9, 2009

(54) *PETUNIA* PLANT NAMED 'SUNSURFCOPAHO'

(50) Latin Name: *Petunia×hybrida*
Varietal Denomination: Sunsurfcopaho

(75) Inventors: Yasuko Isobe, Shiga (JP); Takeshi Kanaya, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/077,200

(22) Filed: Mar. 17, 2008

(51) Int. Cl.
*A01H 5/00* (2006.01)

(52) U.S. Cl. ..... Plt./356

(58) Field of Classification Search ..... Plt./356
See application file for complete search history.

*Primary Examiner*—S. B McCormick Ewoldt
(74) *Attorney, Agent, or Firm*—C. A. Whealy

(57) ABSTRACT

A new and distinct cultivar of *Petunia* plant named 'Sunsurfcopaho', characterized by its trailing plant habit; vigorous growth habit; freely branching and flowering plant habit; long flowering period; small-sized white-colored flowers with yellow green-colored venation; and good garden performance.

1 Drawing Sheet

Botanical designation: *Petunia×hybrida.*
Cultivar denomination: 'Sunsurfcopaho'.

BACKGROUND OF THE INVENTION

The present invention relates to a new and distinct cultivar of *Petunia,* botanically known as *Petunia×hybrida* and hereinafter referred to by the name 'Sunsurfcopaho'.

The new *Petunia* is a product of a planned breeding program conducted by the Inventors in Higashiomi, Shiga, Japan. The objective of the breeding program is to create new *Petunia* cultivars with attractive foliage and flower coloration.

The new *Petunia* originated from a cross-pollination made by the Inventors in August, 2003 in Higashiomi, Shiga, Japan of a proprietary selection of *Petunia×hybrida* identified as code number P1216, not patented, as the female, or seed, parent with the *Petunia×hybrida* cultivar Sunpatiki, disclosed in U.S. Plant Pat. No. 16,297, as the male, or pollen, parent. The new *Petunia* was discovered and selected by the Inventors as a single flowering plant within the progeny of the stated cross-pollination in a controlled environment in Higashiomi, Shiga, Japan.

Asexual reproduction of the new *Petunia* by terminal cuttings in a controlled environment in Higashiomi, Shiga, Japan since September, 2005, has shown that the unique features of this new *Petunia* are stable and reproduced true to type in successive generations.

SUMMARY OF THE INVENTION

The cultivar Sunsurfcopaho has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Sunsurfcopaho'. These characteristics in combination distinguish 'Sunsurfcopaho' as a new and distinct cultivar of *Petunia:*

1. Compact and trailing plant habit.
2. Vigorous growth habit.

3. Freely branching and flowering plant habit.
4. Long flowering period.
5. Small-sized white-colored flowers with yellow green-colored venation.
6. Good garden performance.

Plants of the new *Petunia* can be compared to plants of the female parent selection. Plants of the new *Petunia* differ from plants of the female parent selection in the following characteristics:

1. Plants of the new *Petunia* are not as broad as plants of the female parent selection.
2. Plants of the new *Petunia* and the female parent selection differ in flower color as plants of the female parent selection have white-colored flowers.

Plants of the new *Petunia* can be compared to plants of the male parent, the cultivar Sunpatiki. Plants of the new *Petunia* differ from plants of the cultivar Sunpatiki in the following characteristics:

1. Plants of the new *Petunia* are more compact and more trailing than plants of the cultivar Sunpatiki.
2. Plants of the new *Petunia* have longer internodes than plants of the cultivar Sunpatiki.
3. Plants of the new *Petunia* have longer leaves than plants of the cultivar Sunpatiki.
4. Plants of the new *Petunia* have smaller flowers than plants of the cultivar Sunpatiki.
5. Plants of the new *Petunia* and the cultivar Sunpatiki differ in flower color as plants of the cultivar Sunpatiki have pale yellow green-colored flowers with lime green-colored venation.
6. Plants of the new *Petunia* have smaller sepals than plants of the cultivar Sunpatiki.

Plants of the new *Petunia* can also be compared to plants of the cultivar Keiwhihus, disclosed in U.S. Plant Pat. No. 18,089. In side-by-side comparisons conducted in Higashiomi, Shiga, Japan, plants of the new *Petunia* and the cultivar Keiwhihus differed in the following characteristics:

1. Plants of the new *Petunia* had smaller flowers than plants of the cultivar Keiwhihus.

2. Flowers of plants of the new *Petunia* and the cultivar Keiwhihus differed slightly in color as flowers of plants of the cultivar Keiwhihus had yellowish white-colored flowers.

BRIEF DESCRIPTION OF THE PHOTOGRAPHS

The accompanying colored photographs illustrate the overall appearance of the new *Petunia,* showing the colors as true as it is reasonably possible to obtain in colored reproductions of this type. Colors in the photographs may differ slightly from the color values cited in the detailed botanical description which accurately describe the colors of the new *Petunia.*

The photograph at the top of the sheet comprises a top perspective view of a typical flowering plant of 'Sunsurfcopaho' grown in a container.

The photograph at the bottom of the sheet is a close-up view of typical flowers of 'Sunsurfcopaho'.

DETAILED BOTANICAL DESCRIPTION

The aforementioned photographs and following observations, measurements and values describe plants grown in Higashiomi, Shiga, Japan, under commercial practice during the summer in an outdoor nursery day temperatures averaging 23° C. and night temperatures averaging 13° C. Plants had been growing for about four months when the photographs and description were taken. In the following description, color references are made to The Royal Horticultural Society Colour Chart, 2001 Edition, except where general terms of ordinary dictionary significance are used.

Botanical classification: *Petunia×hybrida* cultivar Sunsurfcopaho.

Parentage:

*Female, or seed, parent.*—Proprietary selection of *Petunia×hybrida* identified as code number P1216, not patented.

*Male, or pollen, parent.*—*Petunia×hybrida* cultivar Sunpatiki, disclosed in U.S. Plant Pat. No. 16,297.

Propagation:

*Type.*—By terminal cuttings.

*Time to initiate roots.*—About one week at temperatures of 20° C. to 25° C.

*Time to produce a rooted young plant.*—About three weeks at temperatures of 20° C. to 25° C.

*Root description.*—Fine, fibrous, fleshy; light brown in color.

*Rooting habit.*—Freely branching.

Plant description:

*Plant and growth habit.*—Compact and trailing plant habit. Freely branching habit with about 17 lateral branches developing per plant; pinching enhances lateral branch development. Vigorous growth habit.

*Plant height.*—About 14 cm.

*Plant diameter.*—About 51 cm.

Lateral branch description:

*Length.*—About 30.3 cm.

*Diameter.*—About 2 mm.

*Internode length.*—About 2 cm.

*Strength.*—Strong, flexible.

*Aspect.*—Obliquely upright.

*Texture.*—Pubescent.

*Color.*—Close to 145B.

Foliage description:

*Arrangement.*—Before flowering, alternate, simple; after flowering, opposite, simple.

*Length.*—About 3.8 cm.

*Width.*—About 1.3 cm.

*Shape.*—Narrowly elliptic.

*Apex.*—Acute.

*Base.*—Attenuate.

*Margin.*—Entire.

*Texture, upper and lower surfaces.*—Pubescent.

*Venation pattern.*—Pinnate; reticulate.

*Color.*—Developing and fully expanded foliage, upper surface: Close to 137B; venation, close to 145B. Developing and fully expanded foliage, lower surface: Close to 138B; venation, close to 145B.

*Petiole.*—Length: About 4.2 mm. Diameter: About 1.9 mm. Texture, upper and lower surfaces: Sparsely pubescent. Color, upper and lower surfaces: Close to 145B.

Flower description:

*Flower arrangement and habit.*—Single salverform flowers arising from leaf axils. Freely flowering habit with usually about 29 open flowers per plant. Flowers face obliquely upright. Flowers not fragrant.

*Natural flowering season.*—Plants of the new *Petunia* initiate and develop flowers about three to four weeks after planting. Long flowering period; flowering commences naturally during the spring and plants flower continuously throughout the summer until late autumn in Japan. Flowers not persistent.

*Flower longevity.*—Individual flowers last about seven to ten days on the plant.

*Flower diameter.*—About 3.9 cm.

*Flower length* (*depth*).—About 3.6 cm.

*Throat diameter.*—About 7.5 mm.

*Tube diameter, base.*—About 2.5 mm.

*Tube length.*—About 2.3 cm.

*Flower bud.*—Shape: Cylindrical. Length: About 3.4 cm. Diameter: About 6.7 mm. Color: Close to 145B.

*Corolla.*—Arrangement: Five petals fused at the base and opening into a flared trumpet. Petal length from throat: About 1.6 cm. Petal width: About 1.9 cm. Petal shape: Spatulate. Petal apex: Mucronate. Petal margin: Entire, undulate. Petal texture, upper and lower surfaces: Smooth, glabrous; velvety. Throat texture: Smooth, glabrous. Tube texture: Sparsely pubescent. Color: Petal, when opening, upper surface: Close to 155A; venation, N144B. Petal, when opening, lower surface: Close to 155A; midvein, close to 144C; lateral veins, close to 151C. Petal, fully opened, upper surface: Close to 155A; venation, N144C. Petal, fully opened, lower surface: Close to 155A; midvein, close to 144C; lateral veins, close to 151C. Throat: Close to 153D; venation, close to N144B. Tube: Close to 150D; venation, close to N144D.

*Calyx.*—Arrangement: One star-shaped calyx tube with five sepals fused at the base per flower. Sepal length: About 7 mm. Sepal width: About 2.1 mm. Sepal shape: Narrowly elliptic. Sepal apex: Obtuse. Sepal margin: Entire. Sepal texture, upper and lower surfaces: Pubescent. Color, upper and lower surfaces: Close to 144A.

*Peduncles.*—Length: About 1.1 cm. Diameter: About 1.3 mm. Strength: Strong. Texture: Sparsely pubescent. Color: Close to 144A.

*Reproductive organs.*—Stamens: Quantity/arrangement: Five per flower. Stamen length: About 1.7 cm to 2.1 cm. Anther shape: Ellipsoidal. Anther size: About 1.5 mm by 2.5 mm. Anther color: Close to 2D. Pollen amount: Moderate. Pollen color: Close to 2D. Pistils: Quantity: One per flower. Pistil length: About 1.8 cm. Style color: Close to 144D. Stigma shape: Transversely ellipsoidal. Stigma color: Close to 143B. Ovary color: Close to 143C.

*Seed/fruit.*—Seed and fruit development have not been observed on plants of the new *Petunia.*

Garden performance: Plants of the new *Petunia* have been observed to have good garden performance and to tolerate rain, wind and temperatures ranging from about 5° C. to about 35° C.

Pathogen/pest resistance: Plants of the new *Petunia* have not been observed to be resistant to pests and pathogens common to *Petunia.*

It is claimed:

1. A new and distinct *Petunia* plant named 'Sunsurf-copaho' as illustrated and described.

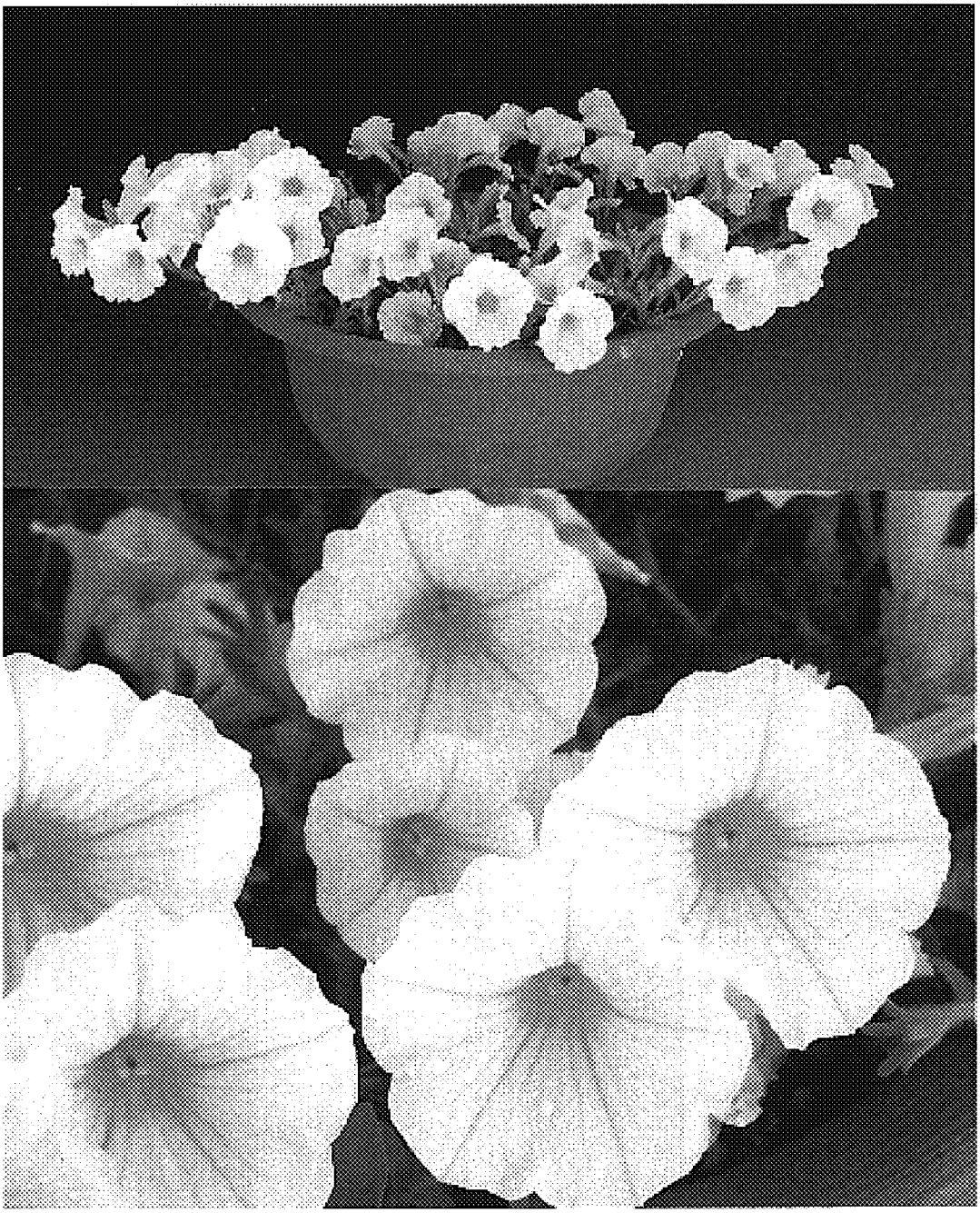

* * * * *